United States Patent [19]
Prusa et al.

[11] Patent Number: 6,133,321
[45] Date of Patent: Oct. 17, 2000

[54] METHOD FOR THE REDUCTION OF STRESS IN MEAT PRODUCING ANIMALS AND MEAT PRODUCED FROM SLAUGHTERED ANIMALS TREATED THEREBY

[75] Inventors: Kenneth J. Prusa, Ames; Christine A. Fedler, Nevada, both of Iowa; Dennis Henley; Leonard Huskey, both of Greeley, Colo.

[73] Assignee: Swift & Company, Greeley, Colo.

[21] Appl. No.: 09/196,538

[22] Filed: Nov. 20, 1998

[51] Int. Cl.$^7$ .................................................. A61K 31/137
[52] U.S. Cl. ........................... 514/653; 424/438; 119/712
[58] Field of Search ............................ 514/653; 424/442, 424/438; 119/712

[56] References Cited

U.S. PATENT DOCUMENTS

| | | | |
|---|---|---|---|
| 2,351,614 | 6/1944 | Hills et al. | 99/107 |
| 2,516,923 | 8/1950 | Schotte et al. | 99/107 |
| 2,992,927 | 7/1961 | Radouco-Thomas | 99/107 |
| 3,042,529 | 7/1962 | Radouco-Thomas | 99/107 |

OTHER PUBLICATIONS

*Veterinary Pharmaceuticals & Biologicals* 76/77 Le Clair ed Acepromazine p. 15–34.

Milks Practical Veterinary Pharmacology, p. 182–185, 196, 1949.

Blakely et al The Science of Animal Husbandry pp. 236, 240, 1976.

Animal Science 7th Edition Ensminger p. 793, 1977.

Teternik et al Diagnosis of Pre–Killing Stress in Slaughter Cattle Myasnaya Industriya SSSR #6 39, 40, 1975.

Hedrick, H.B., et al., "Effect of Adrenaline Stress on Pork Quality," Journal of Animal Science, 1964, 23:225–229.

Fernandez, X., et al., "Effect of Epinephrine Administration on Glycogen Metabolism in Red and White Muscle of Anaesthetized Pigs (*Sus scrofa domesticus*)," J. Sci. Food Agric. 1995, 68, 231–239.

Aberle, et al., "Physical and Biochemical Properties of Porcine Muscle as Affectd by Exogenous Epinephrine and Prednisolone," vol. 33 (1968)—Journal of Food Science, pp. 43–47.

Fernandez, et al., "Effect of Time between Adrenaline Injection and Slaughter on the Rate and Extent of Post–Mortem Metabolism in Porcine Skeletal Muscle," Meat Science 31 (1992) 287–298.

Sconberg, et al., "Effects of Shipping, Handling, Adrenocorticotropic Hormone, and Epinephrine on alpha–tocopherol Content of Bovine Blood," Am J Vet Res, vol. 54, No. 8, Aug. 1993, 1287–1293.

Nockels, et al., "Vitamin E Supplementation and Stress Affect Tissue alpha–Tocopherol Content of Beef Heifers," J. Anim. Sci. 1996. 74:672–677.

Kannan, et al., "Effects of Crating and Transport on Stress and Meat Quality Characteristics in Broilers," 1997 Poultry Science 76:523–529.

Apple, et al., "Effects of Restraint and Isolation Stress and Epidural Blockade on Endocrine and Blood Metabolite Status, Muscle Glycogen Metabolism, and Incidence of Dark–Cutting Longissimus Muscle of Sheep," J. Anim. Sci. 1995. 73:2295–2307.

Swayne, et al., "Sudden Death Syndrome in Turkey Hens," Avian Diseases 34:770–774, 1990.

Hatton, et al., "Effects of Preslaughter Adrenalin Injection on Muscle Metabolites and Meat Quality of Pigs," J. Fd.Technol. (1972) 7, 443–453.

*Primary Examiner*—Neil S. Levy
*Attorney, Agent, or Firm*—Pretty, Schroeder & Poplawski

[57] ABSTRACT

A method of reducing the stress in meat producing animals and of improving the quality of the meat produced from slaughtering said animals, while reducing the number of animals lost due to incapacitation, injury, or untimely death, by administering to the animals an effective amount of epinephrine or an epinephrine-like drug sufficient to acclimate the animal, and allowing the animal then to rest before loading the animal to be slaughtered by industry standard procedures for such meat producing animals. This method produces a meat with high sensory qualities.

6 Claims, No Drawings

METHOD FOR THE REDUCTION OF STRESS IN MEAT PRODUCING ANIMALS AND MEAT PRODUCED FROM SLAUGHTERED ANIMALS TREATED THEREBY

FIELD OF INVENTION

This invention relates to methods for the reduction of stress in meat producing animals, for example, the stress associated with the movement of meat producing animals from the production facility to the point of slaughter in the processing facility, and to the meat obtained from such animal. In particular, the invention relates to a method to reduce or eliminate stress associated with the loading, transporting, unloading, and driving of meat producing animals to be slaughtered, and to the meat obtained from such animal.

BACKGROUND OF THE INVENTION

In the process of moving meat producing animals from the production facility to the packing plant, animals are removed from the holding area (coop, pen, barnyard, etc.), moved down a narrow alleyway, and driven through a loading chute onto a livestock trailer. Animals are then transported for a variable number of hours to a packing facility where they are unloaded from the livestock trailer. The meat producing animals then are moved to a scale, weighed, often tattooed or branded, and moved to a holding area (coop, pen, barnyard, etc.). After a rest period of a variable number of hours, the meat producing animals then are moved into the slaughter area. This process of moving meat producing animals usually is quite stressful to them. Many stressed meat producing animals walk slowly, thus getting in the way of other meat producing animals, while some of the stressed meat producing animals exhibit extreme responses resulting in their inability to move or even death.

Moreover, the sensory qualities of the meat from meat producing animals that were stressed prior to slaughter are not as high as they would otherwise have been, all other factors being equal. Typically this is because more of the animal's muscle glycogen is broken down to glucose than with an unstressed animal. Subsequent metabolism of the glucose results in the formation of lactic acid. Lactic acid formation causes the pH of the muscle cell to drop. In living animals, the lactic acid is metabolized, thus causing the pH to return to normal, higher levels. If the excess lactic acid is not removed from the muscle cells, for example because the animal has been slaughtered, or if the bloodstream is not able to handle the excess lactic acid, a generalized acidosis may occur. If severe, acidosis may lead to death of a living animal.

In animals that already are dead (whether of natural causes, stress-induced reactions, or humane slaughter), an excess of lactic acid, if not removed from the cells, will cause the muscle pH to drop, thus causing the meat to taste and look less desirable. The industry-wide average pH of slaughtered meat producing animals is approximately 5.75 after 24 hours ("ultimate pH"). The pH of animals that have experienced a stress reaction shortly before death is typically in the range of 5.3–5.4 or even lower. Many researchers have attempted to increase the pH of animal meat by various methods, and some have used epinephrine.

It is well known in the art that hormones from the adrenal gland can have a strong influence on animal metabolism and homeostasis. Adrenal hormones help animals to cope with stress through a series of reactions that increase circulation and help provide energy to the muscles. Epinephrine is one of the major adrenal hormones. The natural release of epinephrine readies the animal for stressful situations. Epinephrine binds to the muscle cell, and stimulates the breakdown of glycogen into energy rich compounds, allowing the animal's normal metabolism to dissipate the lactic acid before the animal is slaughtered.

No one previously has been able to acclimate a meat producing animal headed for slaughter in an easy, economical, and efficient manner such that the group of animals so acclimated include fewer slow-walkers and prematurely dead animals, and the animals from a group that have been so acclimated yield meat that is consistently of high quality in terms of taste and appearance. No one previously has been able to produce animal meat with a pH consistently higher than 6.3. In an un-treated group of pigs, for example, very few will have a pH higher than 6.3, while many will have a pH in the 5.5 range.

Accordingly, there has been a long-felt need for a solution to this problem. No one has yet developed a commercially viable solution that can be used by farmers and slaughterers. Moreover, the federal Food and Drug Administration has not yet approved the regular use of epinephrine or epinephrine-like drugs in meat producing animals to reduce stress.

An additional benefit of acclimating the meat producing animals prior to the stress-inducing event is that often stress causes livestock (such as pigs, cattle, and poultry, for example) to shed salmonella. By avoiding the stress reaction, the meat produced by the claimed method will be less contaminated with salmonella.

DISCUSSION OF THE RELATED ART

Adding supplemental levels of epinephrine to swine by injection was the subject of U.S. Pat. No. 2,351,614 issued to C. H. Hills and H. O. Halvorson. That patent discloses a technique of injecting epinephrine (preferably between 0.15 to 0.4 mg per kg of body weight—well above the approved levels used today in pigs) intramuscularly into pigs approximately three hours before slaughter. This process increased muscle pH and decreased the amount of raw muscle exudate and the amount of juice cooked out of ham.

Other studies, have used epinephrine as a technique to study differences in fiber types, metabolic function, and biochemical properties of post-mortem muscle (Hedrick, et al., 1964; Aberle and Merkel, 1968; Hatton, et al., 1972; Fernandez et al., 1992; Fernandez, et al., 1995). For example, in the 1995 study by Fernandez, et al., the researchers anesthetized non-market weight pigs to compare the effect of epinephrine on red and white muscle fibers. Although the researchers "assumed that . . . epinephrine administration in conscious animals influences the general behavior," this theory was never tested nor proved because the researchers used anesthetized pigs. Consequently, no stress reaction in the pigs could have occurred, particularly because the anesthetized animals were not allowed to wake up after the experiment.

SUMMARY OF THE INVENTION

This invention involves a method of reducing the stress in a meat producing animal and of improving the quality of the meat produced from slaughtering said animal, while reducing the number of animals lost due to incapacitation, injury, or untimely death. In accordance with the inventive method, an effective amount of epinephrine or an epinephrine-like drug sufficient to acclimate the animal is administered to the animal and the animal is then rested before loading the animal for slaughter.

Normally, animals are allowed to feed up until the time they are loaded for slaughtering. This provides current food that can be converted into energy, particularly when the "fight-or-flight" reaction is triggered by a stressful event.

In some embodiments of this invention, the meat producing animal is removed from feed prior to loading the animal for slaughter, for anywhere up to 36 hours before slaughter. In a preferred embodiment the animal is removed from feed between 18 to 24 hours before slaughter.

Also in a preferred embodiment, the epinephrine or the epinephrine-like drug is administered by injection, and most preferably if administered by subcutaneous injection. The amounts typically range between 7 and about 37 mcg of epinephrine per 1 kg of animal weight, with a preferred amount of 22 mcg of epinephrine for an animal who has been off feed for about 24 hours, and a preferred amount of as high as about 37 mcg of epinephrine for an animal who has not been off feed, each quantity being per 1 kg of animal weight. The epinephrine or epinephrine-like drug may be administered, or injected, up to about 24 hours before the animal is to be slaughtered. The longer the period of time, the better, but good results have been achieved by administering the epinephrine or epinephrine-like drug between 12 and 24 hours before the animal is to be slaughtered. In preferred embodiments, the meat producing animal is rested for approximately one hour after the injection of said epinephrine.

Our method anticipates that the industry standard procedures for slaughtering such meat producing animals will be used.

DETAILED DESCRIPTION OF THE PREFERRED EMBODIMENTS

The inventive method disclosed herein may be useful with any meat producing animal. The method is particularly useful with meat producing animals from the group that includes pigs, sheep, lambs, cattle, veal, turkeys, or chickens.

Epinephrine is one catecholamine of a group of aromatic amines that effect the heart, the peripheral circulation, and particularly, the metabolism. Epinephrine is the main hormone released by the adrenal medulla that helps the body cope with acute stress. This stress reaction is commonly known as the "fight-or-flight" response. Epinephrine has been approved by the FDA for use in treating anaphylactic shock in meat producing animals. For this reason, the inventive method was tested on meat producing animals by the administration of epinephrine. It is expected that the method will work equally well with other epinephrine-like drugs that affect metabolism when animals are faced with the "fight-or-flight" response to a stressful stimulus.

The amount of drug administered to the meat producing animal must be sufficient to acclimate the animal, that is, to cause the metabolic changes that occur during the "flight-or-flight" response to occur in the animal, as a result of the administration of the epinephrine or the epinephrine-like drug. One such metabolic affect is to dissipate the lactic acid that collects in muscle tissue as a result of the metabolism of glucose after an increase in the animal's metabolism of the stored glycogen.

While epinephrine and epinephrine-like drugs may be administered by a variety of methods, we have found that subcutaneous injection is preferable, because it is fairly easy for the farmers and/or slaughterers to perform, enables the required biological effect, and does not contain the risks inherent with intravenous or intramuscular injection. Moreover, the method of performing the injection does not require any specialized training beyond that which most farmers and slaughterers have received pertaining to other injections typically given to meat producing animals.

This invention involves the administration of a small amount of epinephrine or an epinephrine-like drug to meat producing animals, preferably by subcutaneous injection, ideally approximately one hour before a potentially stressful event, for example, the process of loading such animals to travel to the slaughterhouse. After the injection, the animals are allowed to rest, and then are loaded as normal. The supplemental amount of epinephrine, or such drug, acclimates the animal, and the animal metabolizes a portion of the stored energy in its muscle cells. The preferred method of the injection (subcutaneous) allows for a slower and more efficient utilization (versus intravenous or intramuscular) of epinephrine or such drug. The epinephrine or epinephrine-like drug slowly activates the animal's own defense mechanism against stress prior to encountering the stressful situation.

In a preferred embodiment of this invention, the meat producing animals are withdrawn from feed before slaughter, to lower the amount of new energy sources available to the animal. The amount of time may vary, but in general, longer is better, and best results have been achieved at times as long as 24 hours. As a result of this short fasting period, when the meat producing animal is subjected to the loading, transportation, and slaughter process, the animal has no food in its stomach, and therefore has less available energy for the response to stressful stimuli. This causes the animal to be much calmer and less excitable during loading, transportation, and driving to the slaughter area in the plant. The meat producing animal so treated is much less likely to exhibit acidosis which may lead to incapacitation or death. Also, since the animal is calmer, it is less likely to become injured during movement.

Our method of reducing the stress in meat producing animals, and of improving the quality of the meat from slaughtering said animals, while reducing the number of animals lost due to incapacitation, injury, or untimely death, may be accomplished by removing the meat producing animal from feed up to 24 hours before slaughter; between 3 and 18 hours before the animal is to be slaughtered, administering to the meat producing animal between 7 and about 37 mcg of epinephrine per 1 kg of animal weight; allowing the animal to rest after the injection of epinephrine; and slaughtering the animal following the industry standard procedures for said meat producing animal.

Very good results will be achieved if the meat producing animal is removed from feed approximately 18 hours before slaughter, and administered approximately 22 mcg of epinephrine per 1 kg of animal weight approximately 12 hours before the animal is to be slaughtered.

The meat producing animal may be selected from the group consisting of pig, sheep, lamb, cattle, veal, turkey, or chicken. The animal meat resulting from meat producing animals treated by our method will have muscle fibers with a pH between about 6.3 and 7.0, and regularly above 6.5.

Our method has been tested recently with market weight pigs, under supervision by the United States Department of Agriculture, in a non-laboratory setting, and has achieved outstanding success of an unanticipated dimension. The resultant pig meat has been of an extremely high quality, and has been sold in test markets where it has been received quite favorably. The pig meat from pigs treated by our method has muscle fibers whose pH is regularly between 6.3 and 7.0, and typically above 6.5.

A PREFERRED EMBODIMENT OF THE INVENTION

In a preferred embodiment of this invention, using pigs as a demonstrative example, the following conditions should be met:
1. The market weight pigs to be slaughtered should be removed from feed 18 to 24 hours before slaughter in an attempt to limit the amount of available glucose in the muscle and the bloodstream.
2. At least one hour, but no longer than two hours, before loading starts, the pigs should receive a subcutaneous injection of epinephrine at a dose rate of approximately 22 mcg/kg of body weight.
3. Dose rates of epinephrine may range from 7 to about 37 mcg/kg.
4. The epinephrine injection should be given approximately 12 hours before the animal is to be slaughtered.
5. The pigs should be allowed to rest for up to one hour before loading begins.
6. The pigs should be loaded and transported to the process plant following standard operating procedures.
7. The pigs should be unloaded, weighed, tattooed, and slaughtered at the processing plant following standard operating procedures.

EXAMPLES AND EXPERIMENTAL RESULTS

Example 1

Improvement in Ease of Loading Market Weight Pigs

Market weight pigs, selected from a major Southern Minnesota swine-producing company, were removed from feed approximately 24 hours before slaughter.

Approximately 12 hours before slaughter and 1 hour before loading, selected pigs were given a subcutaneous injection (22 mcg/kg) of epinephrine. Injections were given in the jowl area with an 18 gauge, ⅝ inch long needle.

The selected pigs were allowed to rest for approximately 1 hour before loading onto the livestock trailer.

Additional pigs in the same barn were not injected with epinephrine, and served as controls.

The loading crew was blinded to the experiment. Pigs were loaded using normal handling conditions.

Loading scores were given by the loading crew to treated and control groups, including: perceived calmness; sorting out of pen; and movement in the alleyway. Scores ranged from 1 to 10. A "1" signifies a pig that was not calm, sorted out of the pen with difficulty, and did not move well in the alleyway on the way to the truck. A "10" signifies an extremely calm pig, who sorted out of the pen with ease, and moved down the alleyway with ease.

Results of the loading score evaluation are presented:

| Parameter | Controls (n = 545) | Treated (n = 577) |
| --- | --- | --- |
| perceived calmness | 7 | 8 |
| sorting out of pen | 6 | 9 |
| movement in alleyway | 5 | 9 |

In summary, pigs that were treated were easier to sort out of the pen and moved much better in the alleyway. Treatment had a marginal improvement on the perceived calmness of the pigs.

Example 2

Reduction of Incapacitation During Loading and Shipping of Pigs

Evaluation period was from Jun. 16, 1998 through Aug. 19, 1998.

Market weight pigs, selected from a major Southern Minnesota swine-producing company, were removed from feed approximately 24 hours before slaughter.

Approximately 12 hours before slaughter and 1 hour before loading, selected pigs were given a subcutaneous injection (22 mcg/kg) of epinephrine. Injections were given in the jowl area with an 18 gauge, ⅝ inch long needle.

Pigs were allowed to rest for approximately 1 hour before loading onto the livestock trailer.

Additional similar pigs in the same barn and other barns marketed on the same day were not injected with epinephrine and served as controls.

The loading crews were blinded to the experiment. The pigs were loaded using normal handling conditions.

The pigs were transported to a major Southern Minnesota packing facility.

Upon arrival, the number of pigs from treated and control loads that died on the truck (DOA's) and number of pigs that showed evidence of incapacitation (subject pigs) were recorded. Incapacitated (subject) pigs were defined as those that had difficulty moving off the truck and were not able to adequately walk to the scale. Evidence of incapacitation included injury, tremors, labored breathing, difficulty in movement, or staggered gait.

Results are presented below:

| Parameter | Controls | Treated | % Improvement |
| --- | --- | --- | --- |
| Number of pigs evaluated | 21233 | 8525 | — |
| Number of DOA's | 48 | 6 | |
| Percentage of DOA's | 0.23% | 0.07% | 70% |
| Number of subject pigs | 83 | 27 | — |
| Percentage of subject pigs | 0.39% | 0.32% | 18% |

Treatment resulted in a dramatic reduction of DOA's and a significant decrease in subject pigs.

Example 3

Improvement of Pork Quality Via Stress Reduction With Epinephrine

Market weight pigs, selected from a large Minnesota swine-producing company, were removed from feed approximately 24 hours before slaughter.

Approximately 12 hours before slaughter, and 1 hour before loading, selected pigs were given subcutaneous injections of 0.0 mcg/kg, 9 mcg/kg, 18 mcg/kg, 27 mcg/kg or 35 mcg/kg of epinephrine. Injections were given in the jowl area with an 18 gauge, ⅝ inch long needle.

Pigs were allowed to rest for approximately 1 hour before loading onto the livestock trailer. Pigs were loaded using normal handling conditions and were transported to a major Minnesota packing facility.

Pigs were identified within dosage group, penned, and allowed to rest overnight before slaughter. Pigs were slaughtered the following morning, following standard operating procedures.

Carcasses were segregated into a separate cooler and allowed to chill for approximately 24 hours. Ultimate pH (24 hr) of the loin muscle was measured the following morning.

Results are presented below:

| Dose (mcg/kg) | 0 | 9 | 18 | 27 | 35 |
|---|---|---|---|---|---|
| Parameter | | | | | |
| Number of pigs | 50 | 50 | 50 | 50 | 50 |
| Average pH (24 hr) | 5.91 | 6.12 | 6.17 | 6.49 | 6.63 |
| % Loins pH ≧ 6.8 | 0.0 | 0.0 | 4.0 | 12.9 | 37.9 |
| % Loins pH ≧ 6.5 | 0.0 | 10.0 | 6.0 | 51.7 | 69.7 |
| % Loins pH ≧ 6.2 | 6.0 | 32.0 | 46.0 | 85.9 | 84.7 |

Ultimate pH increased as epinephrine dosage increased. Even the 9 mcg/kg increased the percentage of loins above 6.2. Greater dosages dramatically increased the percentage of loins with an ultimate pH above 6.2, 6.5, and 6.8.

Loins of average pH and loins with high pH were selected for additional meat quality testing.

Additional pork quality tests were performed on pigs with average and high ultimate pHs, including:

percent purge: amount of liquid lost from the meat cut in the vacuum package bag, after a specified storage time.

L*: measured with a Hunterlab calorimeter, L* is the lightness/darkness of the loin, measured by the amount of light reflected from the surface of the meat samples. Darker samples produce lower values, lighter samples produce greater values.

cook loss: amount of weight lost during cooking, calculated from weights of the meat sample before and after cooking.

tenderness: judged by a trained sensory panel on a 1 to 10 scale with 1 that is equal to very tough to 10 that is equal to very tender.

flavor: judged by a trained sensory panel on a 1–10 point scale with 1 that is equal to no pork flavor to 10 that is equal to intense pork flavor.

off-flavor: any flavor in the meat sample not characteristic of fresh pork judged by a trained sensory panel on a 10 point scale.

Results are presented below:

| Parameter | Average-pH (5.72) Pork | High-pH (6.85) Pork |
|---|---|---|
| purge (%) | 2.40 | 0.05 |
| L* (color) | 52.77 | 41.71 |
| cook loss (%) | 20.96 | 12.84 |
| tenderness | 6 | 9 |
| pork flavor | 2 | 7 |
| off-flavor | 5 | 1 (none) |

High-pH pork produced less purge and cook loss, was darker in color, was more tender and flavorful and contained no off-flavors when compared with average-pH pork. All of these parameters point to the fact that high-pH pork is superior in quality in comparison with average-pH pork.

Example 4

Enhancement of Epinephrine Meat Quality Effect with Feed Withdrawal

Market weight pigs were selected from a large Minnesota swine-producing company.

Twenty pigs were removed from feed approximately 24 hours before slaughter and twenty pigs were removed from feed approximately 12 hours before slaughter.

Approximately 12 hours before slaughter, and 1 hour before loading, each pig was given a subcutaneous injection of 22 mcg/kg of epinephrine. The injections were given in the jowl area with an 18 gauge, ⅝ inch long needle.

Each of the pigs was allowed to rest for approximately 1 hour before loading onto the livestock trailer. The pigs were loaded using normal handling conditions, and were transported to a major Minnesota packing facility.

The pigs were identified within each feed withdrawal group, penned, and allowed to rest overnight before slaughter. The pigs were slaughtered the following morning following standard operating procedures.

The porcine carcasses were segregated into a separate cooler and allowed to chill for approximately 24 hours. The ultimate pH (24 hr) of the loin muscle was measured the following morning. Results are presented below:

| Dose Feed Withdrawal | 22 mcg/kg 12 hours | 22 mcg/kg 24 hours |
|---|---|---|
| Parameter | | |
| Number of pigs | 21 | 20 |
| Average pH (after 24 hrs) | 6.22 | 6.39 |
| % Loins pH ≧ 6.5 | 9.5 | 35.0 |
| % Loins pH ≧ 6.2 | 52.4 | 80.0 |

The ultimate pH of the loins was enhanced by a longer feed withdrawal period. The longer feed withdrawal period increased the percentage of loins with pH's greater than pH 6.2 and pH 6.5.

We claim:

1. A method of reducing the stress in meat producing animals, while reducing the number of animals lost due to incapacitation, injury, or untimely death, comprising the steps of:

removing the meat producing animal from feed up to 24 hours before slaughter;

administering to the meat producing animal between 7 and about 37 mcg of epinephrine per 1 kg of animal weight by subcutaneous injection between 12 and 24 hours before the animal is to be slaughtered;

and allowing the animal to rest after the injection of the epinephrine.

2. The method of claim 1, wherein said meat producing animal to be slaughtered is:

removed from feed 12 to 24 hours before slaughter;

administered between 17 and 28 mcg of epinephrine per 1 kg of animal weight;

administered said epinephrine approximately 12 hours before the animal is to be slaughtered;

and allowed to rest for approximately one hour after the injection of epinephrine.

3. The method of claim 1, wherein said meat producing animal is selected from the group consisting of pig, sheep, lamb, cattle, veal, turkey, or chicken.

4. The method of claim 1, wherein said meat producing animal to be slaughtered is:

- removed from feed approximately 18 hours before slaughter;
- administered approximately 22 mcg of epinephrine per 1 kg of animal weight;
- administered said epinephrine approximately 12 hours before the animal is to be slaughtered;
- allowed to rest for approximately one hour after the injection of epinephrine.

5. The method of claim 4, wherein said meat producing animal is selected from the group consisting of pig, sheep, lamb, cattle, veal, turkey, or chicken.

6. The method of claim 5, wherein said meat producing animal is a pig.

* * * * *